United States Patent [19]
Wiltrout et al.

[11] Patent Number: 5,061,488
[45] Date of Patent: Oct. 29, 1991

[54] FLAVONE-8-ACETIC ACID AND INTERLEUKIN-2 FOR CANCER THERAPY

[75] Inventors: Robert H. Wiltrout, Frederick; Ronald L. Hornung, Union Bridge, both of Md.

[73] Assignee: The United States of America, as represented by the Secretary of the Department of Health & Human Services, Washington, D.C.

[21] Appl. No.: 533,442

[22] Filed: Jun. 5, 1990

Related U.S. Application Data

[63] Continuation of Ser. No. 182,222, Apr. 15, 1988.

[51] Int. Cl.$^5$ ...................... A61K 31/35; A61K 45/05
[52] U.S. Cl. .................................... 424/85.2; 514/456
[58] Field of Search .................. 514/456; 424/95, 85.2

[56] References Cited

PUBLICATIONS

Chemical Abstracts 99: 175594t (1983).
Rosenberg et al., The N. England J. of Med., Apr. 9, 1987, vol. 316; No. 15, pp. 889-897.

Primary Examiner—Stanley J. Friedman
Attorney, Agent, or Firm—Birch, Stewart, Kolasch & Birch

[57] ABSTRACT

A treatment regimen for cancer comprises administering to a patient an effective amount of a combination of interleukin 2 and flavone-8-acetic acid. The treatment regime is particularly effective in the treatment of renal cracinoma.

11 Claims, 1 Drawing Sheet

FLAVONE-8-ACETIC ACID AND INTERLEUKIN-2 FOR CANCER THERAPY

This application is a continuation of copending application Ser. No. 07/182,222, filed on Apr. 15, 1988.

FIELD OF THE INVENTION

The present invention relates to a treatment regimen for cancer therapy, and, more particularly, to a treatment regimen for renal carcinoma.

BACKGROUND OF THE INVENTION

Attempts have been made recently to develop immunotherapies for the treatment of cancer based on stimulating the host immune response to the tumor. These approaches were based on attempts to immunize against specific tumor cells or with nonspecific stimulants in the hope that general immune stimulation would concomitantly increase the host antitumor response. Although some experimental evidence indicated that this approach might be feasible in the therapy of established tumors, the inability to stimulate sufficiently strong responses to putative tumor antigens and the general immunoincompetence of the tumor bearing host argued against the success of this approach.

An alternative therapeutic approach to the immunologic treatment of cancer is that of the adoptive transfer of immune cells. Adoptive immunotherapy is defined as the transfer to the tumor-bearing host of active immunologic reagents, such as cells with antitumor reactivity that can mediate, either directly or indirectly, antitumor effects. Adoptive immunotherapy represents an attractive approach to cancer therapy and to other conditions related to immune dysfunction. Because active immunologic reagents are transferred to the host, complete host immunocompetence is not required. Thus, the immunosuppression generally associated with the tumor bearing state does not represent a major problem to this therapeutic alternative. Since host immunocompetence is not required, and in fact may be beneficial to the effects of the adoptive transfer of immune cells, adoptive immunotherapy can be easily combined with other therapies such as chemotherapy and radiation therapy. Since the transferred reagents are immunologically specific, this treatment modality predicts a high degree of specificity and consequently a low morbidity. Further, in contrast to most other therapies, no immunosuppression is likely to result from this treatment.

A review of previous attempts to perform adoptive immunotherapy of cancer in animals and humans can be found in Rosenberg et al.; 1977 *Adv. Cancer Res.* 25: 323–388.

Recent studies have demonstrated that the adoptive transfer of specifically immune or broadly cytotoxic lymphocytes generated in the presence of human recombinant interleukin 2 (rIL2) can result in the regression of established tumors in mice and humans. Similarly, the administration of rIL2 alone, in the absence of adoptive immunotherapy, also has been shown to produce some antitumor effects in mice and humans. However, the use of adoptive immunotherapy and rIL2 to treat cancer patients is a complicated, expensive, and toxic form of therapy.

The disadvantage of the use of large amounts of rIL2 either by itself or in combination with adoptive immunotherapy induces a variety of severe and dose-limiting toxic side effects. Therefore, much attention has recently focused on alternative strategies that could exploit the therapeutic benefits of rIL2 while decreasing the expense and logistic difficulties associated with adoptive immunotherapy, as well as decreasing the toxic sequelae associated with high-dose rIL2 therapy.

Renca murine renal cancer has successfully been treated by a therapeutic regimen which combines doxorubin hydrochloride (DOX) and adoptive immunotherapy (AIT) with rIL2, as described in Salup et al., *J. Immunol.* 138: 641 (1987) and Salup et al., *Cancer Res.*, 46: 3358 (1986). This approach has the advantage of requiring daily administration of a moderate amount of rIL2 rather than the larger amounts required to demonstrate therapeutic effects with rIL2 alone.

SUMMARY OF THE INVENTION

It is an object of the present invention to overcome deficiencies in the prior art, such as noted above.

It is another object of the present invention to provide an improved regimen for treating cancer.

It is a further object of the present invention to provide an improved regimen for treating renal cancer.

Yet another object of the invention is to provide for improved cancer therapy.

The present invention provides a method and regimen for treating cancer comprising administering flavone-8-acetic acid and recombinant human interleukin 2 (rIL2).

According to the present invention, the investigational drug, flavone-8-acetic acid, potently augments the NK activity in the spleen, liver, lungs, and peritoneum in a dose-dependent manner following intravenous or intraperitoneal administration. Combined treatment of established cancers with flavone-8-acetic acid and recombinant human interleukin 2 results in up to 80% long-term survival, while the use of flavone-8-acetic acid or recombinant interleukin 2 alone was unable to induce any long-term survival. The use of the combination of flavone-8-acetic acid and recombinant interleukin 2 provides significant antitumor efficacy using subtoxic doses of rIL2 even without accompanying adoptive immunotherapy.

DETAILED DESCRIPTION OF THE INVENTION

Figure 1A:
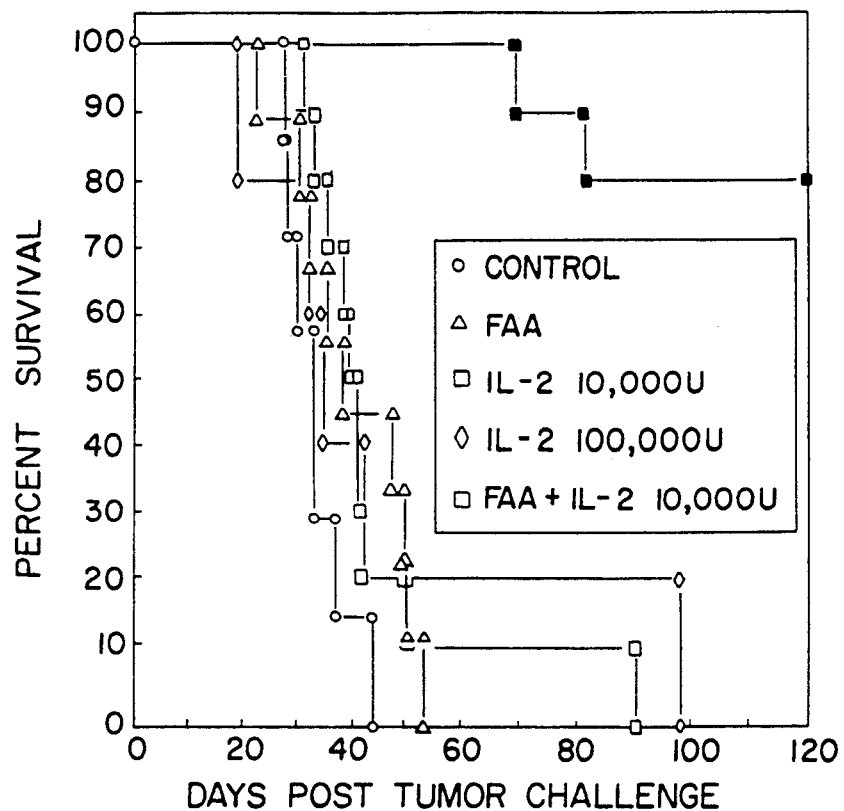
FIG. 1 shows the effect of treatment with flavone-8-acetic acid and/or rIL2 on the survival of Renca-bearing mice.
FIG. 1B shows the control group of mice, who received no flavone-8-acetic acid or rIL2.

According to the present invention, a treatment regimen for cancer is provided to enhance the effectiveness of interleukin therapy. The flavone-8-acetic acid is desirably administered by bolus injection, continuous infusion, or delivery from an osmotic pump in close proximity to the administration of IL2 by any of the above routes to treat cancer in rodents and humans. The doses of flavone-8-acetic acid and IL2 used and the route of administration and the carriers and/or adjuvants used may vary based on the tumor type being treated and in view of known procedures for treatment of such tumors. The combination of flavone-8-acetic acid and IL2 provides synergistic antitumor activity.

Flavone-8-acetic acid was initially selected for clinical testing in cancer patients based upon an unusual spectrum of activity against murine solid tumors which were refractory to conventional chemotherapeutic agents, and favorable preclinical pharmacologic and toxicologic profiles.

It was found that the administration of flavone-8-acetic acid results in a potent systemic augmentation of NK activity, as well as that the combination of flavone-8-acetic acid plus rIL2 exhibits dramatically improved therapeutic effects, comparable to those achieved previously with chemotherapeutic drugs and adoptive immunotherapy against renal cancer.

In all of the experiments described below, male BALB/C mice were housed under specific pathogen free conditions and were used routinely at 7–10 weeks of age.

The flavone-8-acetic acid (FAA) was synthesized by Lyonnaise Industrielle Pharmaceutique.

The rIL2 ($3 \times 10^6$ BRMP units per mg protein) was supplied by Cetus Corporation, Emeryville, Calif.

Polyinosinic-polycytidylic acid and poly-L-lysine stabilized in carboxymethyl cellulose (poly ICLC) was provided by the National Institute of Allergy and Infectious diseases of Frederick, Md.

All reagents were diluted in Hanks Balanced Salt Solution (HBSS) for administration to the mice.

Augmentation of NK activity by FAA was assessed in a four hour $^{51}$Cr release assay against the YAC-1 tumor target. Effector leukocytes were isolated from spleen, peritoneal cavity, lungs, and liver as described by Wiltrout et al., J. Exp. Med. 160: 1431 (1984). The NK activity was expressed as lytic units (LU)/$1 \times 10^7$ cells, with one LU being the number of effector cells required to lyse 20% of the target cells. Statistical comparisons in NK activity were performed by Student's T test.

The tumor model utilized for the present studies is the renca renal adenocarcinoma, a tumor which originated spontaneously and which is maintained by serial transplant in BALC/C mice. The growth characteristics of this tumor have been described in detail in Salup et al., J. Immunol. 138: 641 (1987).

The particular Renca line used for the studies reported hereinafter was isolated form a spontaneous liver metastasis derived form the parental line. Following injection of $1 \times 10^5$ tumor cells under the renal capsule, the solid tumor mass develops rapidly with direct extension to the peritoneal cavity by days 7–9 and metastasis to regional lymph nodes and liver shortly thereafter. Surgical resection of the primary tumor-bearing kidney is potentially curative prior to day 8, but not thereafter, when mice succumb to peritoneal carcinomatosis and subsequent metastatic disease.

The FAA was administered by injection of 125 mg/kg intravenously and 125 mg/kg intraperitoneally, while various doses of rIL2 were delivered intraperitoneally. Routinely, FAA was administered two to four hours after nephrectomy of the primary tumor-bearing kidney on day 11, and rIL2 was administered one time per day for four successive days beginning on the day after nephrectomy and FAA treatment. Statistical analysis of the survival data was performed by the $X^2$ test.

Augmentation of NK Activity Following Administration of FAA

Table 1 illustrates that a single intravenous dose of FAA (250 mg/kg), which has been shown previously to be both active against murine solid tumors and relatively nontoxic, strikingly augmented NK activity in the spleen and liver (p<0.01). The maximum enhancement (51.2 and 236 LU, respectively) of NK activity occurred in both tissues by day 1, remained significantly (p<0.01) augmented through day 3, and returned to near background levels by day 6.

Further studies, shown in Table 2, illustrate that NK stimulation (p<0.01–0.001) by FAA was similarly demonstratable in the lungs and peritoneum, and that the effects were dose dependent in all tissues examined.

TABLE I

Augmentation of NK activity in the Spleen and Liver after Administration of FAA

| Treatment | $Lu_{20}/1 \times 10^7$ leukocytes | |
|---|---|---|
| in Vivo* | Spleen | Liver |
| None | 10.3 | <10 |
| FAA (−1d) | 51.2 | 236.0 |
| FAA (−3d) | 34.5 | 150.8 |
| FAA (−6d) | 17.4 | 21.3 |

*FAA (250 mg/kg) was administered i.v. 1, 3, or 6 days prior to the assessment of NK activity in leukocytes isolated from the spleen and liver. All groups consisted of 5 mice and NK activity was assessed against YAC-1.
Significantly greater than control, P < 0.001.
Significantly greater than control, P < 0.01.

TABLE II

Augmentation of NK Activity in Different Sites after Administration of Various Doses of FAA

| Treatment | $Lu_{20}/1 \times 10^7$ leukocytes | | | |
|---|---|---|---|---|
| In Vivo* (Dose) | Spleen | Peritoneum | Liver | Lungs |
| HBSS | <10 | <10 | <10 | <10 |
| Poly ICLC (0.5 mg/kg) | 64.2 | 137.4 | 211.7 | 84.3 |
| FAA (250 mg/kg) | 56.4 | 108.2 | 103.4 | 39.9 |
| FAA (125 mg/kg) | 37.6 | 94.8 | 20.1 | 10.2 |
| FAA (25 mg/kg) | <10 | 76.1 | <10 | ND |

*BRM were administered i.v. (for assessment of NK activity in spleen, liver, and lungs) or i.p. (for assessment of NK in the peritoneum) 24 hrs. prior to the isolation of effector leukocyte. All groups consisted of 5 mice and NK activity was assessed against YAC-1.
Significantly greater than control, p < 0.001.
Significantly greater than control, p < 0.01.

Treatment of Murine Renal Cancer by FAA and/or rIL2

FIG. 1 shows the effect of treatment with FAA and/or rIL2 on the survival of Renca-bearing mice. BALB/C mice, 8–10 per group, were injected intrarenally with $1 \times 10^5$ Renca tumor cells on day 0. On day 11, the tumor-bearing kidney was removed and 2–4 hours later 125 mg/kg FAA was administered intravenously and 125 mg/kg FAA was administered intraperitoneally to appropriate groups.

Subsequently, beginning on day 12, some of the FAA pretreated mice and two groups of previously untreated mice received four daily intraperitoneal injections of rIL2 at doses of either 10,000 U or 100,000 U/day, as shown in FIG. 1A.

Figure 1B:
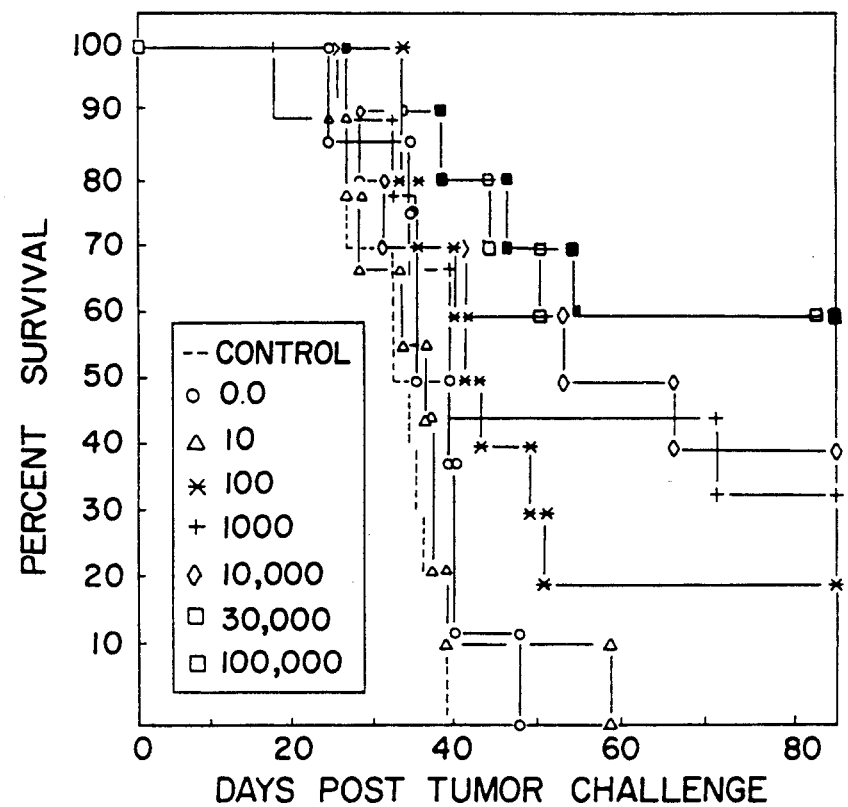

Alternatively, FAA treated mice received increasing doses of rIL2 ranging from 10 U to 100,000 U, as shown in FIG. 1B. The control group in FIG. 1B, represented by the dotted line, received no FAA or rIL2. Mice were then monitored for survival and statistical analyses were performed by the X2 test.

Since 250 mg.kg of FAA markedly enhanced NK activity both in lymphoid and in nonlymphoid sites, as shown in Tables 1 and 2, and NK cells constitute a major precursor for lymphokine-activated killer activity (LAK) generated by rIL2, experiments were performed to determine whether FAA and rIL2 could have additive or synergistic antitumor activity when used in combination.

FIG. 1A shows that a single bicompartmental administration of FAA alone (125 mg/kg intravenously plus 125 mg/kg intraperitoneally) or multiple daily intraperitoneal administrations of either 10,000 U or 100,000 U of rIL2 alone only slightly prolonged the survival of Renca-bearing mice.

In contrast, the combination of FAA and 10,000 U of rIL2 rendered 80% of the tumor-bearing mice free of grossly visual disease through 120 days. Moreover, when FAA-treated mice were tested with a range of daily doses of rIL2, long-term survivors were obtained with as little as 100–100 U rIL2 per day (5/19 survivors), as shown in FIG. 1B.

The survival curve is statistically significantly improved over the control curve at doses of rIL2 $\geq$ 1000 U/mouse. Significantly improved long-term survival was observed for 1000 U ($P<0.05$). 10,000 U ($P<0.05$), 30,000 U ($P<0.005$), and 100,000 U ($P<0.005$).

Overall, these results demonstrate that the use of FAA in association with moderate doses of rIL2 affords appreciably improved long-term survival of mice bearing murine renal cancer as compared to treatment with either FAA or rIL2 alone.

The intravenous and/or intraperitoneal administration of therapeutic c=doses of FAA, ranging from about 110 mk/kg of body weight to about 500 mg/kg of body weight, resulted in potent augmentation of the rIL2 in the spleen or liver. Peak levels of NK-mediated lysis were generally achieved by 24 hour post injection, with levels of NK activity decreasing to background by about day 6.

According to the present invention, the administration of FAA in association with moderate doses of rIL2 appears to be a more useful approach to the treatment of cancer than administration of high doses of rIL2 alone. Recent studies have also shown that the combination of FAA and rIL2 is also effective in eradiating established experimental hepatic metastases, and that the inclusion of adoptive immunotherapy in the treatment regimen does not further increase survival.

The mechanism by which FAA and rIL2 complement each other in the treatment of cancer is not known. The augmentation of NK activity by FAA is an indirect effect, since this agent does not boost NK activity in mice or humans in vitro. Thus, it appears likely that the induction of NK activity, and perhaps the therapeutic effects thereof, are mediated by metabolites of FAA or by cytokines induced by FAA.

The FAA and rIL2 can conveniently be administered intravenously or intraperitoneally, in a suitable carrier.

Carriers which can be used in the present invention include suitable pharmaceutically acceptable carriers comprising excipients and auxiliaries which facilitate processing of the active compounds into preparations which can be used pharmaceutically. Solutions for administration intraperitoneally or intravenously contain from about 0.1 to about 99.5 percent by weight, and preferably from about 25–85 percent by weight, of active ingredient, together with the excipient.

Suitable formulations for parenteral, intraperitoneal, or intravenous administration of the active compounds may include suspensions of the active ingredients as appropriate oily injection suspensions. Suitable lipophilic solvents or vehicles include fatty oils, for example sesame oil, or synthetic fatty acid esters, such as ethyl oleate or triglycerides. Aqueous injection suspensions may contain substances which increase the viscosity of the suspension such as sodium carboxymethylcellulose, sorbitol, or dextran.

The FAA is preferentially administered by bolus injection, continuous infusion, or delivery from an osmotic pump in close proximity to the administration if rIL2 by any of the above routes. The optimal dose of rIL2 required for use with FAA is in the range of about 5,000 to 50,000 U/day, along with about 100 to about 500 mg/kg body weight of FAA.

The FAA can be administered in advance of the administration of the rIL2 by about one day. The rIL2 can be administered one time per day for at least four days beginning after the FAA treatment.

While the invention is described above in relation to certain specific embodiments, it will be understood that many variations are possible, and that alternative materials and reagents can be used without departing from the invention. In some cases such variations and substitutions may require some experimentation, but such will only involve routine testing.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. A synergistic method for treating a cancer in a host, wherein the cancer has cells which are susceptible to an interleukin-2 activated killer cell mediated anticancer effect, the method comprising administering by injection, separately to the host, but in close proximity in time, the following:
   an effective amount of flavone-8-acetic acid for treating the cancer, and
   an effective amount of interleukin 2 for treating the cancer.

2. The method of claim 1, wherein the flavone-8-acetic acid is administered intravenously or intraperitoneally to the host and the interleukin 2 is administered intravenously or intraperitoneally to the host.

3. The method of claim 2, wherein the flavone-8-acetic acid is administered to the host first.

4. The method of claim 3, wherein the administration of flavone-8-acetic acid precedes the administration of interleukin 2 by about one day.

5. The method of claim 3, wherein after the flavone-8-acetic acid is administered, the interleukin 2 is administered one time per day for at least four days.

6. A therapeutic kit for use in the treatment of a cancer having cells which are susceptible to an interleukin-2 activated natural killer cell mediated anti-cancer effect, the kit comprising the following spacially separate components:
   an effective amount of flavone-8-acetic acid for treating the cancer, in a pharmaceutical carrier; and
   an effective amount of interleukin 2 for treating the cancer, in a pharmaceutically acceptable carrier.

7. The kit of claim 6, wherein the kit contains at least one dose of flavone-8-acetic acid and at least four separate doses of interleukin 2.

8. A synergistic pharmaceutical composition comprising an effective amount of flavone-8-acetic acid, and an effective amount of interleukin 2, and a pharmaceutically acceptable carrier.

9. A synergistic method for treating a renal carcinoma in a rodent or a human, said method comprising administering by injection to said rodent or human, an effective renal carcinoma treating amount of flavone-8-acetic acid, and an effective renal carcinoma treating amount of interleukin 2.

10. The method of claim 9, wherein a rodent is treated for a renal carcinoma.

11. The method of claim 9, wherein a human is treated for a renal carcinoma.

* * * * *